United States Patent
Haag et al.

(10) Patent No.: US 10,047,230 B2
(45) Date of Patent: Aug. 14, 2018

(54) BIOINERT ARTICLE AND ITS USE

(71) Applicant: FREIE UNIVERSITÄT BERLIN, Berlin (DE)

(72) Inventors: Rainer Haag, Berlin (DE); Marie Weinhart, Berlin (DE); Qiang Wei, Berlin (DE); Tobias Becherer, Berlin (DE); Ingo Grunwald, Lilienthal (DE)

(73) Assignee: FREIE UNIVERSITÄT BERLIN, Berlin (DE)

( * ) Notice: Subject to any disclaimer, the term of this patent is extended or adjusted under 35 U.S.C. 154(b) by 228 days.

(21) Appl. No.: 15/021,250

(22) PCT Filed: Sep. 8, 2014

(86) PCT No.: PCT/EP2014/069091
§ 371 (c)(1),
(2) Date: Mar. 10, 2016

(87) PCT Pub. No.: WO2015/036364
PCT Pub. Date: Mar. 19, 2015

(65) Prior Publication Data
US 2016/0222224 A1    Aug. 4, 2016

(30) Foreign Application Priority Data

Sep. 13, 2013 (EP) .................................... 13184328

(51) Int. Cl.
*A61F 2/02* (2006.01)
*C09D 5/16* (2006.01)
(Continued)

(52) U.S. Cl.
CPC .......... *C09D 5/1693* (2013.01); *A61F 2/0077* (2013.01); *A61L 27/34* (2013.01);
(Continued)

(58) Field of Classification Search
CPC .. A61F 2/0077; A61F 2002/009; A61L 27/34; A61L 2420/08; C08G 83/006;
(Continued)

(56) References Cited

U.S. PATENT DOCUMENTS 3,271,178 A * 9/1966 Nadeau .................... G03C 1/93
427/171
2003/0087338 A1 5/2003 Messersmith et al.
(Continued)

FOREIGN PATENT DOCUMENTS

DE   10 2011 081260 A1   2/2013
WO      02/060505 A2     8/2002

OTHER PUBLICATIONS

Anderson et al., "The Contribution of DOPA to the Adhesion of Mussel-Inspired Synthetic Peptides", Advance Function Material, vol. 20, No. 23, Dec. 8, 2010, pp. 4196-4205.
(Continued)

*Primary Examiner* — Ashley Fishback
(74) *Attorney, Agent, or Firm* — Maschoff Brennan

(57) ABSTRACT

An article, comprising a substrate and a polymer film attached to the substrate is provided, the polymer film comprising a first layer of a first polymer functionalized by a first functionalization compound covalently bound to said first polymer and bearing at least one catecholic group being present on a surface of the first layer. The polymer film is a layered film, a top layer of which is formed by the first layer, the layered film comprising at least one further layer of at least one further polymer functionalized by a further functionalization compound covalently bound to said further polymer and bearing at least one catecholic group being present on a surface of the at least one further layer, wherein an average ratio of catecholic groups per polymer molecule (Continued)

is equal to or less than 1 in case of the first polymer and greater than 1 in case of the further polymer.

24 Claims, 9 Drawing Sheets

(51) Int. Cl.
  C08G 83/00   (2006.01)
  A61L 27/34   (2006.01)
  C08J 7/04    (2006.01)
  C09D 201/00  (2006.01)
  C09D 201/06  (2006.01)
  C08L 101/00  (2006.01)
  C12M 1/00    (2006.01)
  A61F 2/00    (2006.01)
  C09D 171/00  (2006.01)

(52) U.S. Cl.
  CPC ............ *C08G 83/006* (2013.01); *C08J 7/042* (2013.01); *C08L 101/005* (2013.01); *C09D 171/00* (2013.01); *C09D 201/005* (2013.01); *C09D 201/06* (2013.01); *C12M 23/20* (2013.01); *A61F 2002/009* (2013.01); *A61L 2420/08* (2013.01); *C08J 2300/202* (2013.01)

(58) Field of Classification Search
  CPC ... C08J 7/042; C08J 2300/202; C08L 101/05; C09D 5/1693; C09D 171/00; C09D 201/005; C09D 201/06; C12M 23/20
  See application file for complete search history.

(56) References Cited

U.S. PATENT DOCUMENTS

| | | | |
|---|---|---|---|
| 2008/0149566 A1 | 6/2008 | Messersmith et al. | |
| 2008/0171012 A1 | 7/2008 | Messersmith et al. | |
| 2009/0093610 A1 | 4/2009 | Textor et al. | |
| 2010/0028719 A1 | 2/2010 | Messersmith et al. | |

OTHER PUBLICATIONS

Anderson, J.M., "Biological Responses to Materials", Annual Review of Materials Research, vol. 31, Aug. 2001, pp. 81-110.
Banerjee et al., "Antifouling coatings: recent developments in the design of surfaces that prevent fouling by proteins, bacteria, and marine organisms", Advance Materials, vol. 23, No. 6, Feb. 8, 2011, pp. 690-718.
Chen et al., "Biocompatible polymer materials: Role of protein-surface interactions", Progress in Polymer Science, vol. 33, Issue 11, Nov. 2008, pp. 1059-1087.
Dalsin et al., "Mussel Adhesive Protein Mimetic Polymers for the Preparation of Nonfouling Surfaces", Journal of the American Chemical Society, vol. 125, No. 14, 2003, pp. 4253-4258.
Dalsin et al., "Protein Resistance of Titanium Oxide Surfaces Modified by Biologically Inspired mPEG-DOPA", Langmuir, vol. 21, No. 2, 2005, pp. 640-646.
Drechsel et al., "Peptide siderophores", Journal of Peptide Sceince, vol. 4, No. 3, May 1998, pp. 147-181.
Fan et al., "Biomimetic Anchor for Surface-Initiated Polymerization from Metal Substrates", Journal of the American Chemical Society, vol. 127, No. 45, 2005, pp. 15843-15847.
Fischer et al., "Controlled release of DNA from photoresponsive hyperbranched polyglycerols with oligoamine shells", Macromolecular Bioscience, vol. 11, No. 12, Dec. 8, 2011, pp. 1736-1746.
Franzmann et al., "A Biomimetic Principle for the Chemical Modification of Metal Surfaces: Synthesis of Tripodal Catecholates as Analogues of Siderophores and Mussel Adhesion Proteins", A European Journal Chemistry, vol. 17, Issue 31, Jul. 25, 2011, pp. 8596-8603.
Frazier et al., "Characterization of protein-resistant dextran monolayers", Biomaterials, vol. 29, No. 9, May 2000, pp. 957-966.
Gaines et al., "Evaporation of Langmuir-Blodgett Monolayers in Vacuum", Nature, vol. 197, Feb. 23, 1963, pp. 787.
Gillich et al., "Self-assembly of focal point oligo-catechol ethylene glycol dendrons on titanium oxide surfaces: adsorption kinetics, surface characterization, and nonfouling properties", Journal of the American Chemical Society, vol. 133, No. 28, Jul. 20, 2011, pp. 10940-10950.
Higuchia et al., "Chemically Modified Polysulfone Hollow Fibers with Vinylprrolidone Having Improved Blood Compatibility", Biomaterials, vol. 23, Issue 13, Jul. 2002, pp. 2659-2666.
Jin et al., "Analysis of Steric Hindrance Effects on Adsorption Kinetics and Equilibria", AIChE Journal , vol. 40, Issue 10, Oct. 1994, pp. 1685-1696.
"Kang et al., ""One-Step Modification of Superhydrophobic Surfaces by a Mussel-Inspired Polymer Coating"", Angewandte Chemie International Edition, vol. 49, Issue 49Dec. 3, 2010, pp. 9401-9404".
Lee et al., "Catechol-grafted poly(ethylene glycol) for PEGylation on versatile substrates", Langmuir, vol. 26, No. 6, Mar. 16, 2010, pp. 3790-3793.
Lee et al., "Mussel-inspired surface chemistry for multifunctional coatings", vol. 318, Oct. 19, 2007, pp. 426-430.
Lee et al., "Single-molecule mechanics of mussel adhesion", Proceedings of the National Academy of Sciences of the United States of America, vol. 103, No. 35, Aug. 29, 2006, pp. 12999-13003.
Ling et al., "Multiple-Interaction Ligands Inspired by Mussel Adhesive Protein: Synthesis of Highly Stable and Biocompatible Nanoparticles", Angewandte Chemie International Edition, vol. 50, Issue 48, Nov. 25, 2011, pp. 11360-11365.
Love et al., "Self-assembled monolayers of thiolates on metals as a form of nanotechnology", Chemical Reviews, vol. 105, No. 4, Apr. 2005, pp. 1103-1169.
Ma et al., ""Non-Fouling" Oligo(ethylene glycol)-Functionalized Polymer Brushes Synthesized by Surface-Initiated Atom Transfer Radical Polymerization", Advance Materials, vol. 16, Issue 4, Feb. 2004, pp. 338-341.
Raymond et al., "Enterobactin: An archetype for microbial iron transport", Proceedings of the National Academy of Sciences of the United States of America, vol. 100, Apr. 1, 2003 , pp. 3584-3588.
Reichert et al., "Size-dependant cellular uptake of dendritic polyglycerol", Small, vol. 7, No. 6, Mar. 21, 2011, pp. 820-829.
Rodriguez et al., "Surface Complexation at the TiO(2) (anatase)/Aqueous Solution Interface: Chemisorption of Catechol", Journal of Colloid Interface Science, vol. 177, No. 1, Jan. 15, 1996, pp. 122-131.
Santini et al., "A controlled-release microchip", Nature, vol. 397, Jan. 28, 1999, pp. 335-338.
Siegers et al., "Self-Assembled Monolayers of Dendritic Polyglycerol Derivatives on Gold That Resist the Adsorption of Proteins", A European Journal Chemistry, vol. 10, Issue 11, Jun. 7, 2004, pp. 2831-2838.
Statz et al., "New Peptidomimetic Polymers for Antifouling Surfaces", Journal of the American Chemical Society, vol. 127, Issue 22, 2005, pp. 7972-7973.
Steffensa et al., "High density binding of proteins and peptides to poly(D,L-lactide) grafted with polyacrylic acid", Biomaterials, vol. 23, No. 16, Aug. 2002, pp. 3523-3531.
Subramani et al., "Biocompatible Charged and Uncharged Surfaces Using Nanoparticle Films", Advance Materials, vol. 22, Issue 47, Dec. 14, 2010, pp. 5420-5423.
Sunder et al., "Controlled Synthesis of Hyperbranched Polyglycerols by Ring-Opening Multibranching Polymerization", Macromolecules, vol. 32, No. 13, 1999, pp. 4240-4246.
Sunder et al., "Hyperbranched Polyether Polyols: A Modular Approach to Complex Polymer Architectures", Advance Materials, vol. 12, Issue 3, Feb. 2000, pp. 235-239.

(56) References Cited

OTHER PUBLICATIONS

Waite et al., "Polyphenolic Substance of Mytilus edulis: Novel Adhesive Containing L-Dopa and Hydroxyproline", Science, vol. 212, Issue 4498, Jun. 1981, pp. 1038-1040.
Waite et al., "Polyphosphoprotein from the adhesive pads of Mytilus edulis", Biochemistry, vol. 40, No. 9, Mar. 6, 2001, pp. 2887-2893.
Wei et al., "Improving the blood compatibility of material surfaces via biomolecule-immobilized mussel-inspired coatings", Journal of Biomedical Material Research Part A, vol. 96A, Issue 1, Jan. 2011, pp. 38-45.
Weinhart et al., "Linear and Hyperbranched Polyglycerol Derivatives as Excellent Bioinert Glass Coating Materials", Advanced Engineering Materials, vol. 13, Issue 12, Dec. 2011, pp. B501-B510.
Wnek et al., In Encyclopedia of Biomaterials and Biomedical Engineering (Second Edition), Chapter 229, Informa Healthcare, New York, USA, 2008.
Wyszogrodzka et al., "Synthesis and characterization of glycerol dendrons, self-assembled monolayers on gold: a detailed study of their protein resistance", Biomacromolecules, vol. 10, Issue 5, May 11, 2009, pp. 1043-1054.
Zhang et al., "Blood compatibility of surfaces with superlow protein adsorption", Biomaterials, vol. 29, Issue 32, Nov. 2008, pp. 4285-4291.
Zürcher et al., "Biomimetic Surface Modifications Based on the Cyanobacterial Iron Chelator Anachelin", Journal of the American Chemical Society, vol. 128, No. 4, 2006, pp. 1064-1065.
Malisova et al., Poly(ethylene glycol) Adlayers Immobilized to Metal Oxide Substrates Through Catechol Derivatives: Influence of Assembly Conditions on Formation and Stability, Langmuir, 2010 26 (6), p. 4018-4026.
Gao et al., Functionalizable and ultra-low fouling zwitterionic surfaces via adhesive mussel mimetic linkages, Biomaterials, 2010, 31, p. 1486-1492.
Pop-Georgievski et al., Poly(ethylene oxide) Layers Grafted to Dopaminemelanin Anchoring Layer: Stability and Resistance to Protein Absorption, Biomacromolecules, 2011, 12, p. 3232-3242.
Zhang et al., A facile approach to surface modification on versatile substrates for biological applications, J. Mater. Chem., 2012, 24, p. 6484-6489.
Liu et al., Antimicrobial and Antifouling Hydrogels Formed In Situ from Polycarbonate and Poly(ethylene glycol) via Michael Addition, Adv. Mater., 2012, 24, p. 6484-6489.
Kim et al. Electrospun catechol-modified poly(ethyleneglycol) nanofibrous mesh for anti-fouling properties. J. Mater. Chem. B., 2013, 1, p. 3940-3949.
Di Lullo et al., Mapping the Ligand-binding Sites and Diseaseassociated Mutations on the Most Abundant Protein in the Human, Type I Collagen, J. Biol. CHem., 2002, 277, p. 4223-4231.
Gunkel et al., Cooperative adsorption of lipoprotein phospholipids, triglycerides, and cholesteryl esters are a key factor in nonspecific adsorption from blood plasma to antifouling polymer surfaces. J. Am. Chem. Soc., 2013, 135, 7047. (Abstract Only).
Weinhart et al., Linear poly(methyl glycerol) and linear polyglycerol as potent protein and cell resistant alternatives to poly(ethylene glycol), Chem.-Asian J., 2010, 5, p. 1992. (Abstract Only).

* cited by examiner

BIOINERT ARTICLE AND ITS USE

CROSS-REFERENCE TO A RELATED APPLICATION

This application is a National Phase Patent Application of International Patent Application Number PCT/EP2014/069091, filed on Sep. 8, 2014, which claims priority of European Patent Application Number 13184328.6, filed on Sep. 13, 2013.

BACKGROUND

The invention relates to an article.

An article as described herein has a surface that is modified in order to reduce protein and cell adhesion and can thus be described as antifouling-coated surface.

Biofouling on material surfaces in the biological, medical or diagnostic field is a major problem that can result in inflammation, cell adhesion, irritation of the surrounding tissue, and improper function of devices in vivo and in vitro [1, 1a, 2]. Therefore, improving the bioinert and antifouling ability of material surfaces in contact with biofluids plays an important role, e.g. in medical engineering. Medical implants for example are manufactured from diverse material classes in order to fulfil the specific criteria of their mechanical and biochemical requirements. Polymers, metals, ceramics and others are commonly used for the production of surgical and orthopaedic screws, plates, dental implants, artificial limbs, stents, or drug eluting devices. Some of these are desired to stay inside the body for the lifetime of the patient. However, most materials exhibit a significant degree of bioincompatibility on the long term leading to serious side effects like improper function of devices, in particular biosensors, rejection of implants, and life threatening restenosis of arterial stents.

In order to overcome these issues and to improve the biocompatibility of materials a commonly applied strategy is to coat the surface of the material with a stealth, biocompatible material [3]. Most commonly polyethylene glycol (PEG), a linear polyether polymer which is known since decades to improve the biocompatibility of materials surfaces is employed besides others such as polyvinylpyrrolidone (PVP) [4], oligo(ethylene glycol) (OEG) [5], albumin [6], heparin [7] and dextran [8].

Thereby, single step of monolayer formation [9,10] and multiple step surface modification approaches [11,12] are the most common methods to yield bioinert surfaces. Monolayers are normally created by the chemisorption of head anchors onto substrates followed by a slow organization of the tail groups [13]. Macromolecular tail groups may limit the further adsorption of other feasible adsorbates to form a dense single monolayer due to steric crowding [14].

In addition, the respective bioinert polymer for surface modification has to be modified with a surface specific and reactive anchor that allows for the tethering of the polymer to substrate surface. Unfortunately, despite their comparably easy preparation monolayered coatings often lack stability and easily get destructed. In multiple step surface modification adhesive molecule layers are typically employed, for example poly(ethylene imine) [15] and polydopamine [16, 17] which both are more substrate-independent since they stick to a variety of materials via electrostatic and van-der-Waals interactions to connect the substrates and the bioinert molecules to build up the antifouling coatings.

However, these chemically active adhesive layers show a significant fouling performance most likely due to their charged nature, which is difficult to be completely shielded by grafting bioinert terminal layers on top of it [18,19].

In order to resolve this contradiction between stable coatings on the one hand, and perfectly bioinert surfaces on the other hand, the preparation of stable, highly effective antifouling coatings remains a great challenge, especially when it comes to substrates that are chemically not easy to modify like most polymeric materials.

In the search for antifouling PEG alternatives, polyglycerol (PG) and its derivatives have been identified [20,21] as strong and potent candidates because of their easy accessibility and higher thermal and oxidative stability than PEG. Surface bound hyperbranched polyglycerol (hPG), which has a highly branched architecture consisting of a flexible aliphatic polyether backbone with hydrophilic surface groups, shows similar or better protein resistant performance than PEG-coated surfaces. Gold and glass surfaces have been modified by hPG monolayers and were classified as highly protein-resistant materials [20,21]. But it still remains a challenge to immobilize hPG on a broad range of different material surfaces, like titanium dioxide and commodity plastics, by using the same surface linker group.

One substrate-independent coating approach is bioinspired and based on a mussel adhesive peptide rich in the amino acid L-3,4-dihydroxyphenylalanine (DOPA), an amino acid that bears a catechol motive which is believed to be responsible for both adhesive and crosslinking characteristics [22]. Catechol itself has been proven to be a powerful anchor for surface modification [16,17,23-26]. Catechol groups, which are found in mussel adhesive proteins [22,27] and bacterial siderophores [28,29] can adhere on virtually almost any material surface. Although the mechanistic adhesion details are still not well understood, previous studies have proposed several mechanisms for different kinds of substrates.

Some research has proposed that a charge-transfer complex could be formed between the catechol and a $TiO_2$ surface [30] or that a hydrogen bonding could be formed between the catechol and mica surface [31]. Also van der Waals forces between the catechol and polymer surfaces [32] and covalent bonds on nucleophile containing surfaces have been discussed [33].

At least three catechols are required in the anchor group to effectively and stably immobilize macromolecules on substrates [34,35]. Thus, a number of new catecholic anchor groups have been developed, including 3,4-dihydroxyphenylalanine (DOPA) contained decapeptide [36,37], DOPA short peptides [34,38], pentapeptide of alternating DOPA and lysine residues [24,39], catechol derivatives [40,41], catechol side chains [42], oligo-catechol [35], tripodal catecholates [43], and polyDOPA [44].

It is not easy to prepare these catecholic anchor groups, because they require challenging organic synthesis or solid phase synthesis for the DOPA containing peptides. Thus, so far all catechol bearing anchor groups have been synthesized on a milligram scale only, which is insufficient for many coating applications. In addition, in most cases a coupling step of the bioinert or bioactive compound or polymer to the catecholic anchor moiety is required.

LIST OF REFERENCES CITED IN THE PRECEDING SECTION

[1] J. T. Santini, M. J. Cima, R. Langer, *Nature* 1999, 397, 335.

[1a] J. M. Anderson, *Annual Review of Materials Research* 2001, 31, 81.

[2] C. Subramani, A. Bajaj, O. R. Miranda, V. M. Rotello, *Adv. Mater.* 2010, 22, 5420.
[3] I. Banerjee, R. C. Pangule and R. S. Kane, *Adv. Mater.*, 2011, 23, 690-718.
[4] A. Higuchia, K. Shiranoa, M. Harashimaa, B. O. Yoona, M. Haraa, M. Hattorib, K. Imamura, *Biomaterials* 2002, 23, 2659.
[5] Z. Zhang, M. Zhang, S. F. Chen, T. A. Horbett, B. D. Ratner, S. Y. Jiang, *Biomaterials* 2008, 29, 4285.
[6] G. C. M. Steffensa, L. Nothdurfta, G. Busea, H. Thissenb, H. Hoeckerb, D. Klee, *Biomaterials* 2002, 23, 3523.
[7] H. Chen, L. Yuan, W. Song, Z. K. Wu, D. Li, *Prog. Polym. Sci.* 2008, 33, 1059.
[8] R. A. Frazier, G. Matthijs, M. C. Davies, C. J. Roberts, E. Schacht, S. J. B. Tendler, *Biomaterials* 2000, 21, 957.
[9] J. C. Love, L. A. Estroff, J. K. Kriebel, R. G. Nuzzo, G. M. Whitesides, *Chem. Rev.* 2005, 105, 1103.
[10] G. L. Gaines, R. W. Roberts, *Nature* 1963, 197, 787.
[11] C. Subramani, A. Bajaj, O. R. Miranda, V. M. Rotello, *Adv. Mater.* 2010, 22, 5420.
[12] H. Ma, J. Hyun, P. Stiller, A. Chilkoti, *Adv. Mater.* 2004, 16, 338.
[13] G. E. Wnek, G. L. Bowlin, in *Encyclopedia of Biomaterials and Biomedical Engineering (Second Edition)*, Chapter 229, Informa Healthcare, New York, USA, 2008.
[14] X. Z. Jin, J. Talbot, N. H. L. Wang, AICHE J. 1994, 40, 1685.
[15] C. Subramani, A. Bajaj, O. R. Miranda, V. M. Rotello, *Adv. Mater.* 2010, 22, 5420.
[16] H. Lee, S. M. Dellatore, W. M. Miller, P. B. Messersmith, *Science* 2007, 318, 426.
[17] P. B. Messersmith, H. Lee, US 20080149566 A1, Apr. 26, 2008.
[18] M. Wyszogrodzka, R. Haag, *Biomacromolecules* 2009, 10, 1043
[19] Q. Wei, B. J. Li, N. Yi, B. H. Su, Z. H. Yin, F. L. Zhang, J. Li, C. S. Zhao, *J. Biomed. Mater. Res., Part A* 2011, 96, 38.
[20] C. Siegers, M. Biesalski, R. Haag, *Chem. Eur. J.* 2004, 10, 2831.
[21] M. Weinhart, T. Becherer, N. Schurbusch, K. Schwibbert, H. J. Kunte, R. Haag, *Adv. Eng. Mater.* 2011, 13, B501.
[22] J. H. Waite, M. L. Tanzer, *Science* 1981, 212, 1038.
[23] J. L. Dalsin, B. H. Hu, B. P. Lee, P. B. Messersmith. *J. Am. Chem. Soc.* 2003, 125, 4253.
[24] A. R. Statz, R. J. Meagher, A. E. Barron, P. B. Messersmith. *J. Am. Chem. Soc.* 2005, 127, 7972.
[25] X. W. Fan, L. J. Lin, J. L. Dalsin, P. B. Messersmith. *J. Am. Chem. Soc.* 2005, 127, 15843.
[26] S. Zuercher, D. Waeckerlin, Y. Bethuel, B. Malisova, M. Textor, S. Tosatti, K. Gademann. *J. Am. Chem. Soc.* 2006, 128, 1064.
[27] J. H. Waite, X. X. Qin, *Biochemistry* 2001, 40, 2887.
[28] K. N. Raymond, E. A. Dertz, S. S. Kim, *Proc. Natl. Acad. Sci. U.S.A.* 2003, 100, 3584.
[29] H. Drechsel, G. Jung, *J. Pept. Sci.* 1998, 4, 147.
[30] R. Rodriguez, M. A. Blesa, A. E. Regazzoni, *J. Colloid Interface Sci.* 1996, 177, 122.
[31] T. H. Anderson, J. Yu, A. Estrada, M. U. Hammer, J. H. Waite, J. N. Israelachvili, *Adv. Funct. Mater.* 2010, 20, 4196.
[32] S. M. Kang, I. You, W. K. Cho, H. K. Shon, T. G. Lee, I. S. Choi, J. M. Karp, H. Lee, *Angew. Chem.-Int. Edit.* 2010, 49, 9401.
[33] H. Lee, N. F. Scherer, P. B. Messersmith, *Proc. Natl. Acad. Sci. U.S.A.* 2006, 103, 12999.
[34] J. L. Dalsin, L. Lin, S. Tosatti, J. Voeroes, M. Textor, P. B. Messersmith, *Langmuir* 2005, 21, 640.
[35] T. Gillich, E. M. Benetti, E. Rakhmatullina, R. Konradi, W. Li, A. F. Zhang, A. D. Schlueter, M. Textor, *J. Am. Chem. Soc.* 2011, 133, 10940.
[36] J. L. Dalsin, B. H. Hu, B. P. Lee, P. B. Messersmith, *J. Am. Chem. Soc.* 2003, 125, 4253.
[37] P. B. Messersmith, K. Huang, B. P. Lee, J. L. Dalsin, B. H. Hu, J. Friedstat, US 20030087338 A1, May 8, 2003.
[38] P. B. Messersmith, A. R. Statz, B. P. Lee, J. L. Dalsin, D. Sherman, US 20080171012 A1, Jul. 17, 2008.
[39] P. B. Messersmith, A. E. Barron, A. Statz, N. Chongslriwatana, US 20100028719 A1, Feb. 4, 2010.
[40] S. Zürcher, D. Wäckerlin, Y. Bethuel, B. Malisova, M. Textor, S. Tosatti, K. Gademann, J. Am. Chem. Soc. 2006, 128, 1064.
[41] M. Textor, S. Zürcher, K. Gademann, S. Tosatti, US 20090093610 A1, Apr. 9, 2009.
[42] H. Lee, K. D. Lee, K. B. Pyo, S. Y. Park, H. Lee. *Langmuir* 2010, 26, 3790.
[43] E. Franzmann, F. Khalil, C. Weidmann, M. Schroeder, M. Rohnke, J. Janek, B. M. Smarsly, W. Maison. *Chem.-Eur. J.* 2011, 17, 8596.
[44] D. Ling, W. Park, Y. Park, N. Lee, F. Y. Li, C. Song, S. G. Yang, S. H. Choi, K. Na, T. Hyeon. *Angew. Chem. Int. Ed.* 2011, 50, 11360.

SUMMARY

It is an object of the instant invention to provide a versatile strategy for a stable bioinert coating on various types of substrate surfaces which at the same time show surprising antifouling performance. In particular, an article shall be provided, the surface of which is modified to provide antifouling properties, wherein this surface modification can be applied to virtually all substrate materials.

This object is achieved by an article comprising a substrate and a polymer film attached or bound to the substrate. Thereby, the polymer film comprises a first layer of a first polymer. This polymer is functionalized by a first functionalization compound covalently bound to said first polymer and bearing at least one catecholic group which is—after the polymer has been functionalized by the first functionalization compound—present on a (molecular) surface of the first polymer. In other words, the first functionalization compound serves for introducing a catecholic group into the first polymer, wherein this catecholic group is easily accessible since it is present on the surface of the polymer (and not only in the interior of the polymer). Therewith, this catecholic group is automatically present on a surface of a layer formed by the first polymer.

The claimed article is characterized in that the polymer film is a layered film, a top layer of which is formed by the first layer. In addition, the layered film comprises at least one further layer of at least one further polymer. This further polymer is also functionalized by a further functionalization compound covalently bound to the further polymer. The further functionalization compound also bears at least one catecholic group which in turn is present on a (molecular) surface of the further polymer, after the polymer has been functionalized with the further functionalization compound. Therewith, this catecholic group is automatically present on a surface of a layer formed by the further polymer. Thus, the layered polymer film comprises at least two layers of catechol-functionalized polymers. It also comprises at least two layers on the respective surfaces of which catecholic groups are present. Additionally, an average ratio of catecholic groups per polymer molecule is equal to or less than 1 in case of the first polymer and greater than 1 in case of the further polymer. Since the first polymer builds up the top layer of the layered polymer film, the number of catecholic groups on the surface of the polymer of the top layer is less than the number of catecholic groups on the surface of the polymer building up the further layer or layers of the layered polymer film. The further polymer can also be denoted as additional polymer. In the same way, the further layer and the further functionalization compound can be denoted as additional layer and additional functionalization compound.

In particular, the average ratio of catecholic groups per polymer molecule is, in case of the first polymer, 0.7 to 1.0, in particular 0.8 to 0.9.

The term "catecholic group" comprises all groups having a structural motive according to the following general formula I:

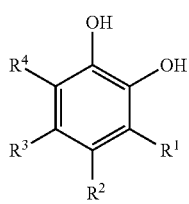

formula I

Thereby, residues $R^1$, $R^2$, $R^3$ and $R^4$ can be absent, hydrogen or any organic or organometallic residue.

Preferred residues are aliphatic or aromatic chains (such as, e.g., $C_1$-$C_{10}$ aliphatic chains or $C_6$-$C_{20}$ aromatic residues) that can optionally be interrupted or substituted by moieties containing nitrogen, oxygen and/or sulfur atoms, e.g., by —$NH_2$, —NH—, —OH, =O, —O—, —SH and/or —S—S—. Specific examples for any of residues $R^1$, $R^2$, $R^3$ and $R^4$ are —$CH_2$—$CH_2$—$NH_2$, —CHOH—$CH_2$—$NH_2$, —$CH_2$—$CH_2$—NH—C=O and —CH($NH_2$)—$CH_2$—$CH_2$—$CH_2$—$CH_2$—$NH_2$.

The catecholic group can be bound to the bare polymer via any of residues $R^1$, $R^2$, $R^3$ and $R^4$ or by a covalent bond that is formed to a carbon atom of the benzene ring of the catecholic group according to general formula I at which any of residues $R^1$, $R^2$, $R^3$ and $R^4$ is bound in formula I. In such a case, the according residue $R^1$, $R^2$, $R^3$ or $R^4$ would be absent. In other words, the catecholic group can be directly bound to the bare polymer. Residues $R^1$, $R^2$, $R^3$ and $R^4$ can have independently from each other the same meaning or different meanings in each case.

In an embodiment, exactly one residue (namely either $R^1$, $R^2$, $R^3$ or $R^4$) is absent, so that a direct link of the catecholic group to the bare polymer is established at this site, whereas the remaining residues are hydrogen. This embodiment corresponds to a direct catechol-functionalization of a bare polymer, like, e.g., polyglycerol.

The term "bare polymer" denotes a polymer without functionalization compound. I.e., the bare polymer of a catechol-functionalized polyglycerol is polyglycerol.

The term "catecholic group" also refers to the oxidized form of catechol and its derivatives that is also known as quinone and corresponds to the following general formula II:

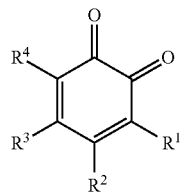

formula II

The residues $R^1$, $R^2$, $R^3$ and $R^4$ can have the same meaning as previously explained. The invention is based on the idea of combining substrate-independent, versatile catecholic anchor groups with a polymer being preferably flexible and bioinert and having preferably a moderate to high functional group density. Thereby, the polymer should preferably offer sufficient attachment points for the catecholic groups by its functional groups and should, in a further embodiment, at the same time provide the option for further modification in order to change its surface properties. The heart of the invention is the new, polymer-based layer architecture of the coating that is hierarchically constructed.

A dual layer architecture can be used in particular on metal or metal oxide surfaces. Dendritic catechol groups can form strong complexes with such surfaces. This architecture can be made by a bioinert crosslinked anchoring layer which may consist of multimolecular layers of polymers, while a sealing top layer is typically a monolayer of the polymer which optionally might provide an option for functionalization.

Triple layer architecture can be used on other surfaces. This architecture can be made by an active crosslinked anchoring layer which can form stable coatings even on Teflon surfaces, and the dual layer mentioned above which can hide the activity of the anchoring layer.

In an embodiment, a lowest polymer layer of the layered polymer film is non-covalently attached to the substrate. The lowest polymer layer is that layer of the layered polymer film that is furthest away from the top layer of the layered polymer film. In case of a two-layered polymer film, the lowest polymer layer is directly beneath the top layer of the polymer film. In case of three-layered polymer films or multi-layered polymer films, the lowest polymer layer is indirectly beneath the top layer of the polymer film. The non-covalent bonding of the lowest polymer layer to the substrate is preferably effected by adhesion of the catecholic groups of the polymer building up the lowest polymer layer to a surface of the substrate. The adhesion can take place by formation of a charge-transfer complex, by hydrogen bonding or by van der Waals forces.

In another embodiment, the lowest polymer layer of the layered polymer film is covalently bound to the substrate. Such covalent bonds can be formed between the catecholic groups of the polymer building up the lowest polymer layer and a nucleophilic surface of the substrate.

In an embodiment, the further polymer is covalently bound to a polymer of a polymer layer of the layered polymer film that is placed directly above the further polymer layer. In case of a two-layered polymer layer, the top layer is placed directly above the further polymer layer. In case of a three-layered polymer film, the top polymer layer is placed directly above an intermediate polymer layer which in turn is placed directly above a lowest polymer layer. In such a case, the polymer forming the lowest polymer layer would be covalently bound to the polymer forming the intermediate polymer layer and this polymer forming the intermediate polymer layer would be covalently bound to the polymer forming the top polymer layer. Such covalent bonding between the polymers can be preferably effected by cohesion, i.e. by cross-linking bonds directly formed between the benzene rings of the involved catecholic groups. Such cohesion-induced bond can be established between two catecholic groups if they are present in the oxidized (quinonic) form as represented in general formula II.

In an embodiment, the further polymer has a degree of functionalization with catecholic groups of 1 to 100%, in particular of 1 to 50%, in particular 5 to 45%, in particular 5 to 40%, in particular 10 to 40%, in particular 15 to 35% and very particular 20 to 30%. The degree of functionalization indicates the number of catechol-functionalized reactive groups of the polymer in relation to the total number of reactive groups of the polymer.

In another embodiment, the first and/or the further polymer is at least one of the group consisting of polyglycerols, in particular linear polyglycerols or branched polyglycerols, polyethers, polyethylene glycols, polyesters, polyamides, polyimides, polyimines, polyurethanes, polycarbonates, polyethersulfones, oligopeptides, polypeptides and copolymers thereof, in each case functionalized by the first or the further functionalization compound.

Thereby, the first polymer can be—apart from the average ratio of catecholic groups per polymer molecule—the same polymer like the further polymer or a different polymer than the further polymer. In the same way, the different further polymers can be built-up from the same bare polymer or can contain different bare polymers.

In an embodiment, the first and/or the further polymer has a bare molecular weight of 0.6 to 6000 kDa. The term "bare molecular weight" refers to the molecular weight of the bare polymer. The term "molecular weight" refers to the number average molecular mass ($M_n$). It can be determined by gel permeation chromatography. In an embodiment, the first and/or the further polymer has a molecular weight after modification of 0.3 to 6000 kDa.

Preferably, the bare molecular weight or the molecular weight after modification (i.e. after functionalization) of the first and/or the further polymer is in the range of 1 to 100 kDa, in particular 2 to 50 kDa and very particular 5 to 10 kDa. The molecular weight of the bare or functionalized first polymer can be identical to the molecular weight of the bare or functionalized further polymer. Alternatively, the molecular weight of the bare or functionalized first polymer and of the bare or functionalized further polymer can be different.

In an embodiment, the first and/or further functionalization compound only consists of a catecholic group as defined above, in particular of a non-derivatized catechol group. In another embodiment, the first and/or the further polymer has a spacer or linker moiety through which a catecholic group is bound to the first and/or the further polymer. This spacer or linker moiety corresponds to any of residues $R^1$, $R^2$, $R^3$ and $R^4$ of the above-depicted general formulae I and II. If, e.g., dopamine is used as functionalization compound, the spacer or linker moiety would be —$CH_2$—$CH_2$—NH—.

In an embodiment, the first and/or the further polymer bears, besides the catecholic groups, reactive groups (such as amine, amide, azide, hydroxyl and/or sulfhydryl groups) that can be functionalized in order to adjust physical and/or chemical surface properties of the article. Such reactive groups can be used to introduce further functionalization compounds into the polymer. In doing so, the first polymer can be functionalized in the same way like the further polymer. Alternatively, the functionalization of the first polymer and the further polymer can be different.

In another embodiment, the first polymer is additionally functionalized with at least one compound selected from the group consisting of polyethylene glycol, oligoethylene glycol, zwitterionic moieties, polyoxazolines, oligooxazolines, and other hydrophilic groups based on amides, amide derivatives, cyclic esters, sugar derivatives, amino acids and/or oligonitrils.

These compounds decrease the non-specific interaction of bio entities with the polymer-coated surface of the article.

In another embodiment, the first polymer is additionally functionalized with at least one compound selected from the group consisting of bioactive units or ligands such as amino acids, peptides, monosaccharides, oligosaccharides, polysaccharides, proteins, DNA and RNA. Enzymes and antibodies are further examples of possible bioactive units or ligands. Aptamers are preferred forms of RNA. All of these bioactive units or ligands initiate a specific interaction of certain addressed bio entities with the surface. Thus, by introducing such bioactive units or ligands, specific interactions with, e.g., surrounding tissue, can be enhanced.

By combining an additional functionalization with at least one compound decreasing the non-specific interaction of bio entities with the surface of the polymer-coated article with an additional functionalization with at least one compound increasing the specific interaction of certain addressed bio entities with the surface of the polymer-coated article, a tailor-made article can be produced that addresses the needs of a specific application of the article.

In another embodiment, the first functionalization compound and the further functionalization compound are identical. If also the first bare polymer and the further bare polymer are identical, the first polymer and the further polymer only distinguish each other with respect to the average ratio of catecholic groups per polymer molecule. Such a design of the first polymer and the further polymer allows easy manufacturing of the article.

In another embodiment, the first functionalization compound and the further functionalization compound are different from each other.

In another embodiment, the layered polymer film has a thickness of 1 nm to 100 μm, in particular 2 to 2000 nm, in particular 5 to 1000 nm, in particular 7 to 100 nm, in particular 9 to 20 nm and very particular 10 to 15 nm.

In another embodiment, the substrate comprises at least one compound chosen from the group consisting of titanium dioxide, aluminum, glass, silicon dioxide, polystyrene (PS), polypropylene (PP) and polyvinyl chloride (PVC).

The present invention also relates to the use of an article as described hereinbefore as device for in vitro cell culture. For example, the article can be a Petri dish that efficiently prevents growing cells from adhering to the material of the Petri dish.

The present invention also relates to the use of an article as described hereinbefore as implantable device or as part of an implantable device. This implantable device can be a device intended for permanent implantation or a device intended for non-permanent implantation. In case of a non-permanent implant, a basic version of the described article (in which the first polymer is not additionally functionalized) is preferred. Additionally, an enhanced version of the described article (in which the first polymer is further functionalized by a compound decreasing non-specific interactions with other bio entities) is preferred.

In case of a permanent implant, an enhanced version of the article (in which the first polymer is additionally functionalized with at least one compound increasing specific interactions with selected bio entities) is preferred. Such additional functionalization can enhance the ingrowth of a permanent implant into the surrounding tissue.

BRIEF DESCRIPTION OF THE DRAWINGS

The present invention will now be described in more detail by referring to exemplary embodiments and corresponding Figures.

DETAILED DESCRIPTION

Figure 1:
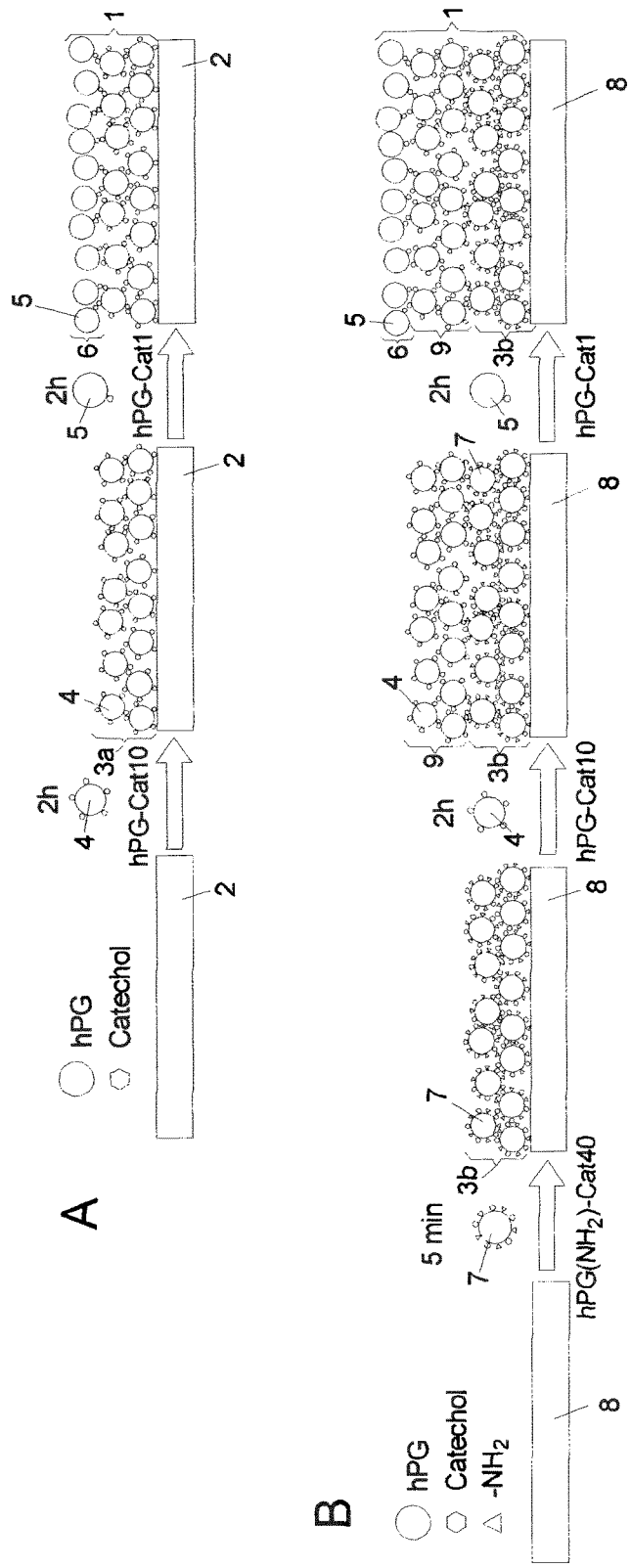
FIG. 1A shows a schematic depiction of a first embodiment of a polymer-coated article.
FIG. 1B shows a schematic depiction of a second embodiment of a polymer-coated article.

FIG. 1A is a schematic depiction of the steps to be performed in order to produce an article coated with an antifouling-coating of a two-layered polymer film 1 on a metal substrate 2. For building up the polymer film 1, a multiple catechol-functionalized hyperbranched polyglycerol (hPG) 4 with a degree of functionalization of 10% (hPG-Cat10) is produced in a first step from hPG and a functionalization compound bearing a catecholic group. This hPG-Cat10 4 was developed to form an inert foundation layer 3a which can effectively shield metals, metal oxides and other substrates. The foundation layer 3a can also be referred to as lowest polymer layer of the layered polymer film 1. The foundation layer 3a is a multi-molecular layer in which the individual catechol-functionalized polyglycerols 4 (which serve as second or further polymer) are cross-linked to each other via their catechol groups. In addition, the catechol groups of the polymer 4 of the foundation layer 3a serves for anchoring the whole foundation layer 3 to metal and metal oxide surfaces by strong complexes.

To build up the foundation layer 3, the according polymer 4 (hPG-Cat10) is incubated with the metal substrate 2 for two hours. In the second reaction step, a mono-catechol functionalized hPG (hPG-Cat1) 5 is applied to the coated metal substrate 2. This hPG-Cat1 serves as terminating molecule forming a terminal top layer 6. hPG-Cat1 5 can also be referred to as first polymer. hPG-Cat1 5 is conjugated on the surface of the inert foundation layer 3a built up by multiple-catecholic hPG-Cat10 4 by catechol cross-linking to hide free catechol groups and to form a stable bioinert surface.

FIG. 1B is a schematic depiction of an article comprising a three-layered polymer film 1 on a substrate 2. The same numeral references as in FIG. 1A will be used for the same elements.

The inventors were able to show that hPG-Cat10 is not perfectly well-suited to adhere on all substrate surfaces. Rather, an adhesion onto metal substrates like the metal substrate 2 takes place with high efficiency. On other surfaces, especially on non-metal surfaces, the stability of the adhesion of hPG-Cat10 can still be improved. Therefore, an hPG was produced which is functionalized with catechols and amines. The catechol functionalization degree of this hPG is 40% and the amine functionalization degree is 60%. This polymer is also referred to as hPG($NH_2$)Cat40 7 and also serves as further polymer functionalized by a catecholic group. hPG($NH_2$)Cat40 7 is a super-adhesive molecule that strongly adheres also on non-metal substrates 8.

In doing so, a multi molecular layer of hPG($NH_2$)Cat40 7 serves as foundation layer 3b or lowest layer of the polymer film 1. In order to build up a bioinert surface coating on the substrate 8, hPG-Cat10 4 is applied as intermediate layer 9 onto the surface of the foundation layer 3b composed of hPG($NH_2$)Cat40 7. Thus, the intermediate layer 9 of this exemplary embodiment corresponds to the foundation layer 3a of the precedingly explained exemplary embodiment (cf. FIG. 1A). The catechol groups of hPG-Cat10 4 form covalent bonds to hPG($NH_2$)Cat40 7. These covalent bonds are formed by crosslinking between the catechol groups of hPG-Cat10 4 and the catechol groups of hPG($NH_2$)Cat40 7 and/or the amine groups of hPG($NH_2$)Cat40 7. In other words, a catechol-catechol coupling or a catechol-amine coupling takes place. Afterwards, a top layer 6 of hPG-Cat1 5 is applied onto the surface of the intermediate layer 9. Once again, a catechol-catechol coupling between the catechol groups of hPG-Cat1 5 and the catechol groups of hPG-Cat10 4 takes place. The top layer 6 of hPG-Cat1 5 seals the lower layers and provides for a bioinert coating of the substrate 8.

Both the foundation layer 3b and the intermediate layer 9 are multi-molecular layers, wherein the top layer 6 is a mono-molecular layer.

When comparing the exemplary embodiment depicted in FIG. 1A and the exemplary embodiment depicted in FIG. 1B, it is obvious that the chosen approach can be used to form a highly stable surface coating on versatile substrates without the need to change the anchoring groups to coat different surface substrates. The cross-linked active foundation layer 3b serves as a multivalent anchor to cover non-metal substrates and to tether the following layer. This following layer, the intermediate layer 9, serves as inert foundation layer placed on top of the active foundation layer 3b. Unlike chemically active layers which are hard to be completely shielded by grafting bioinert terminal layers on top of them, this new inert foundation layer (the intermediate layer 9) can both strongly adhere to metal substrates (and thus act as single inert foundation layer 3a) and strongly adhere to active foundation layers 3b, since it can exhibit multivalent adhesion and intralayer cohesion as well as interlayer layer cohesion. Thus, it can durably resist desorption.

The terminal top layer 6 which is based on the monofunctionalized hPG-Cat1 5 couples to the inert foundation layer 3a or to the intermediate layer 9, both being composed of hPG-Cat10 4, in order to hide all active or sticky catechol functionalities to get an highly optimized bioinert surface. Since catechols (or catecholic groups) have been chosen for both anchors and cross-linkers of the foundation layer 3b, the intermediate layer 9 and the top layer 6, the same chemistry can be used to build up the whole multiple layer architecture coating including anchoring polymers 7, cross-linking polymers 4 as well as terminating polymers 5.

It is obvious from the foregoing explanation that hPG-Cat10 4 and hPG(NH$_2$)Cat40 7 are only examples for anchoring and cross-linking polymers. In the same way, hPG-Cat1 5 is only an example of a terminating polymer. In fact, other bare polymers or other functionalization compounds can be used.

hPG(NH$_2$)Cat40 7 cannot only be used to coat non-metal substrates 8, but also to coat metal substrates 2. In case of metal substrates 2 or metal oxide substrates, it is not necessary to work with a three-layer architecture of the coating to be applied on the substrate. Rather, in this case, a two-layered architecture of the polymer film to be applied on the substrate can be used, as explained in FIG. 1A.

The reactions schematically depicted in FIGS. 1A and 1B have been performed in the following way in order to produce an antifouling-coated article.

First, hPG, with a number average molecular mass (M$_n$) ≈5000 g·mol$^{-1}$ and a mass average molecular mass (M$_w$) ≈7500 g·mol$^{-1}$, was polymerized by a one-step ring-opening anionic polymerization (ROAP), as described by A. Sunder, R. Mühlhaupt, R. Haag, H. Frey, *Adv. Mater.* 2000, 12, 235 and by A. Sunder, R. Hanselmann, H. Frey, R. Mühlhaupt, *Macromolecules* 1999, 32, 4240. Trimethylolpropane (TMP) was used as the initiator or starter. Amine-functionalized hPG and carboxyl-functionalized hPG were prepared according to procedures previously published by S. Reichert, P. Welker, M. Calderón, J. Khandare, D. Mangoldt, K. Licha, R. K. Kainthan, D. Brooks, R. Haag, *Small* 2011, 7, 820 and by W. Fischer, M. A. Quadir, A. Barnard, D. K. Smith, R. Haag, *Macromol. Biosci.* 2011, 11, 1736.

In the case of 1 equivalent and 10% catechol functionalization, catecholic hPGs were synthesized by correspondingly grafting 3,4-dihydroxyhydrocinnamic acid (DHHA) or dopamine to amine functionalized or carboxyl functionalized hPG. In the case of hPG(NH$_2$)Cat40 with 40% catechol and 60% amine functionalization, acetonide protected DHHA was grafted to hPG amine with 100% functional degree, HCl was used for deprotection. The amount of grafted catechols per hPG was confirmed by NMR analysis. The amine amount was determined by NMR and FTIR analysis.

hPG-Cat1 (Yield: 95%)
$^1$H NMR (700 MHz; MeOD): δ=6.69-6.54 (m, 2.71H, C$\underline{H}_{arom.}$); 3.91-3.21 (m, 541.61H, PG-backbone); 2.77 (t, 1.86H, COC$\underline{H}_2$CH$_2$C); 2.46 (t, 1.83H, COC$\underline{H}_2$CH$_2$C); 1.42-1.40 (m, 2H, C$\underline{CH}_2$CH$_3$ of starter); 0.90 (t, 3H, CC$\underline{H}_2$C$\underline{H}_3$, of starter) ppm. $^{13}$C NMR (700 MHz; MeOD): δ=175.92 and 175.59 (C=O); 146.32-112.62 (C$_{arom.}$); 81.70-43.59 (PG backbone); 39.47 and 37.10 (COC$\underline{H}_2$CH$_2$C); 32.49 and 31.90 (COCH$_2$C$\underline{H}_2$C); 23.83 (C$\underline{CH}_2$CH$_3$ of starter); 8.58 (CCH$_2$C$\underline{H}_3$ of starter) ppm.

hPG-Cat10 (Yield: 92%)
$^1$H NMR (700 MHz; MeOD): δ=6.69-6.54 (m, 35.15H, C$\underline{H}_{arom.}$); 3.90-3.22 (m, 541.61H, PG-backbone); 2.77 (m, 23.39H, COC$\underline{H}_2$CH$_2$C); 2.45 (m, 23.27H, COCH$_2$C$\underline{H}_2$C); 1.41-1.39 (m, 2H, C$\underline{CH}_2$CH$_3$ of starter); 0.90 (t, 3H, CCH$_2$C$\underline{H}_3$, of starter) ppm. $^{13}$C NMR (700 MHz; MeOD): δ=175.95 and 175.71 (C=O); 146.31-112.47 (C$_{arom.}$); 81.70-43.55 (PG backbone); 39.39 and 37.09 (COC$\underline{H}_2$CH$_2$C); 32.48 and 31.80 (COCH$_2$C$\underline{H}_2$C); 22.14 (C$\underline{CH}_2$CH$_3$ of starter); 7.09 (CCH$_2$C$\underline{H}_3$ of starter) ppm.

hPG(NH$_2$)Cat40 (Yield: 94%)
$^1$H NMR (700 MHz; MeOD): δ=6.72-6.52 (m, 129.12H, C$\underline{H}_{arom.}$); 4.03-2.97 (m, 541.61H, PG-backbone); 2.75 (m, 85.22H, COC$\underline{H}_2$CH$_2$C); 2.48 (m, 87.09H, COC$\underline{H}_2$CH$_2$C); 1.49-1.39 (m, 2H, C$\underline{CH}_2$CH$_3$ of starter); 0.90 (t, 3H, CCH$_2$C$\underline{H}_3$, of starter) ppm. $^{13}$C NMR (700 MHz; MeOD): δ=176.86 and 176.29 (C=O); 146.31-111.87 (C$_{arom.}$); 81.18-43.55 (PG backbone); 39.13 and 37.57 (COC$\underline{H}_2$CH$_2$C); 32.31 and 31.30 (COCH$_2$C$\underline{H}_2$C); 24.46 (C$\underline{CH}_2$CH$_3$ of starter); 7.26 (CCH$_2$C$\underline{H}_3$ of starter) ppm.

For building dual layer coatings on titanium dioxide surfaces, freshly cleaned slides were immersed with 1 mM hPG-Cat10 in pH 7.5 3-(N-morpholino)propanesulfonic acid (MOPS) buffer (0.1 M) at around 20° C. for 2 hours. After carefully washing, hPG-Cat10 coated slides were immersed with 1 mM hPG-Cat1 in the same conditions.

For building triple layer coatings on polystyrene, freshly cleaned slides were immersed with 0.1 mM hPG(NH$_2$)Cat40 in a mixed solution of methanol and pH 8.5 MOPS buffer (4:1 v/v) for 5 minutes. Then the hPG-Cat10 and hPG-Cat1 coatings were prepared as described above. After coating, the slides were thoroughly rinsed with water and methanol and dried by a N$_2$ stream.

Coating of the titanium dioxide substrates with hPG-Cat10 caused a considerable decrease of the static water contact angle from 67±2° of the bare substrate to 28±3°. In the case of the dual layer architecture, screening the exposed catechol groups of hPG-Cat10 with a terminal layer of hPG-Cat1 further decreased the static water contact angle to 22±2°. Coating of the polystyrene substrates with hPG(NH$_2$)Cat40 for 5 min caused a decrease of the static water contact angle from 83±4° to 53±4°. After further coated by hPG-Cat10Cat1 dual layer to construct the triple layer architecture, the angle dramatically decreased to 20±3°.

Figure 2:
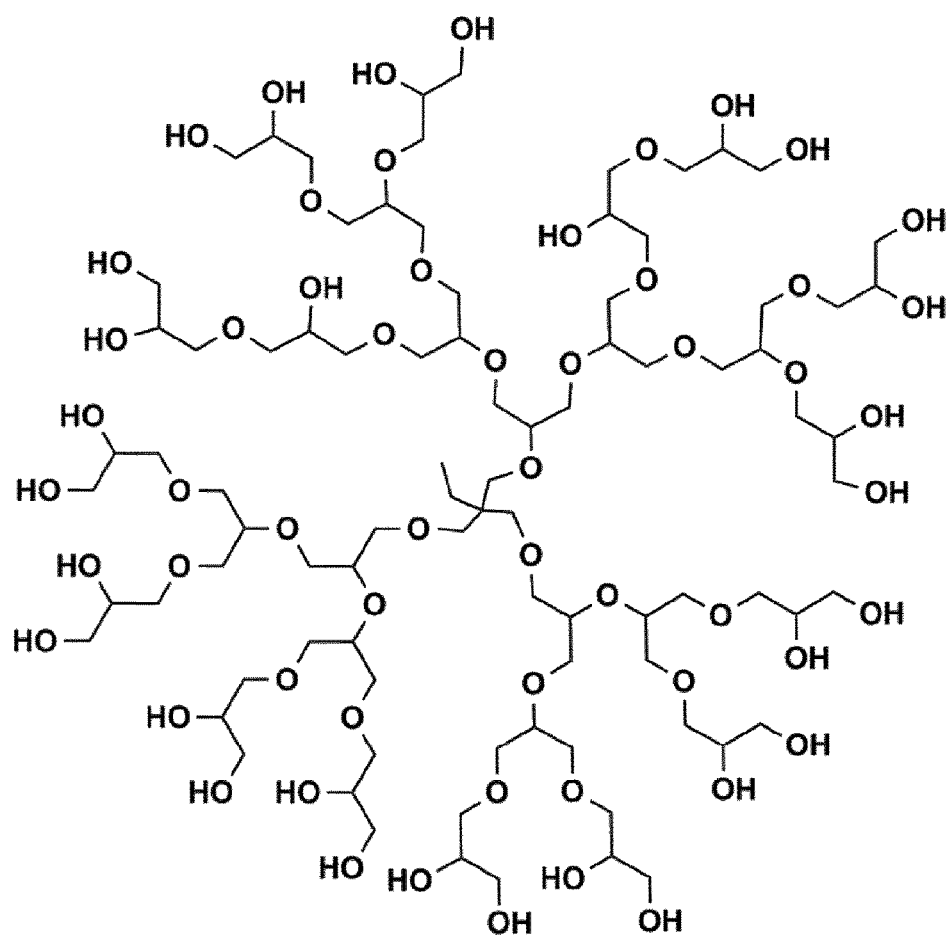
FIG. 2 shows the chemical structure of an exemplary branched polyglycerol that can be used as a bare polymer for the first polymer and/or the further polymer of an embodiment of a polymer-coated article.

FIG. 2 is a schematic depiction of the possible structure of a hyperbranched polyglycerol (hPG). Such hPG can be used as starting point for preparing catecholic hPGs with different degrees of functionalization of catechol units. The functionalization can take place via ester or more stable amide bonds.

The hPG as depicted in FIG. 2 having a number average molecular mass (M$_n$) of approximately 5000 g·mol$^{-1}$ was prepared by a one-step anionic ring-opening polymerization, as described by A. Sunder, R. Mühlhaupt, R. Haag, H. Frey, *Adv. Mater.* 2000, 12, 235 and A. Sunder, R. Hanselmann, H. Frey, R. Mühlhaupt, *Macromolecules* 1999, 32, 4240.

Catecholic hPGs with more stable amide bonds (hPG-Cat) were developed from amine-functionalized hPGs (see S. Reichert, P. Welker, M. Calderón, J. Khandare, D. Mangoldt, K. Licha, R. K. Kainthan, D. Brooks, R. Haag, *Small* 2011, 7, 820).

Catecholic hPGs with ester bonds (hPG-ester-Cat) were produced from carboxyl-functionalized hPGs (see W. Fischer, M. A. Quadir, A. Barnard, D. K. Smith, R. Haag, *Macromol. Biosci.* 2011, 11, 1736). hPG-ester-Cat can be synthesized in just two simple steps from hPG which is beneficial for the synthesis of larger amounts. In rigorous conditions, it is possible to use hPG-Cat with amide bonds. In general, any type of standard conjugation and legation chemistry that is known to the person skilled in the art can be adapted for the synthesis of catechol-functionalized polymers, provided that feasible linkers or spacers are available.

Figure 3A:
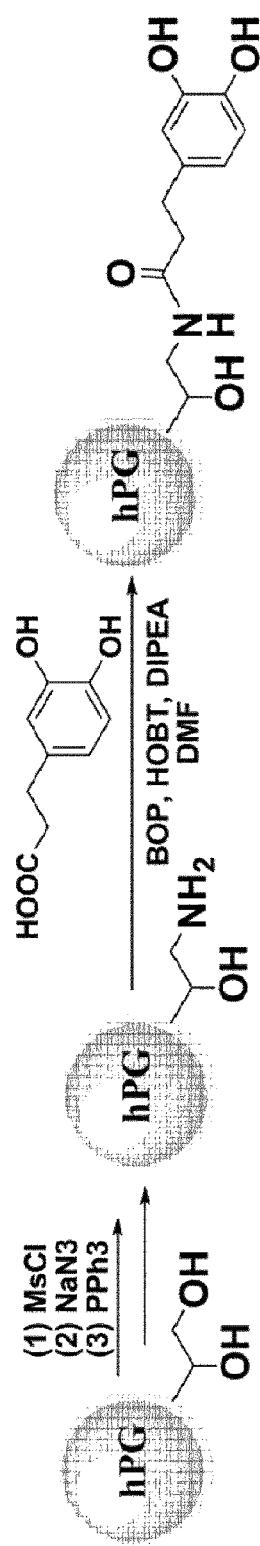
FIG. 3A shows the chemical reaction scheme of a first embodiment of functionalizing a polyglycerol with a functionalization compound bearing a catecholic group.
Figure 3B:
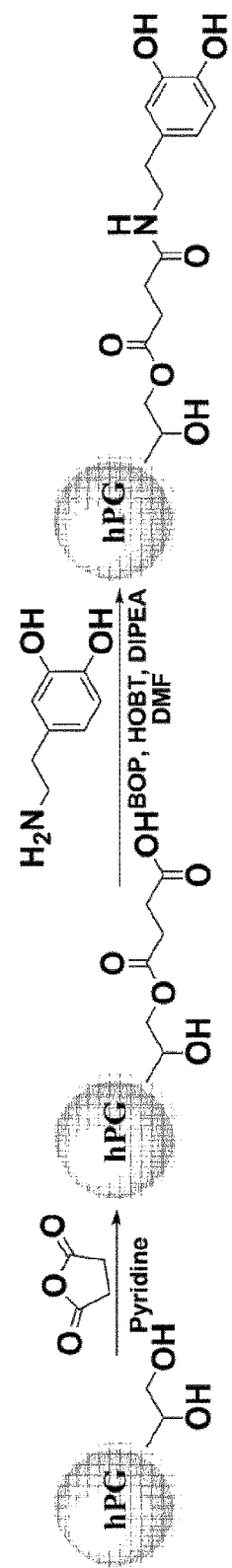
FIG. 3B shows the chemical reaction scheme of a second embodiment of functionalizing a polyglycerol with a functionalization compound bearing a catecholic group.
Figure 3C:
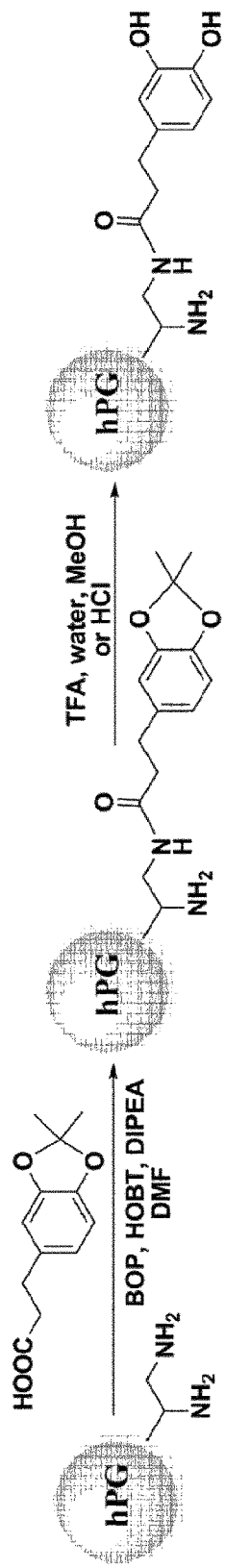
FIG. 3C shows the chemical reaction scheme of a third embodiment for functionalizing a polyglycerol with a functionalization compound bearing a catecholic group.

FIGS. 3A, 3B and 3C show reaction schemes of functionalization reactions of hPGs with different functionalization compounds. In all of these compounds, the catecholic groups are bound to the bare polymer via linker or spacer groups. The functionalization degree of the produced functionalized hPGs can be adjusted, e.g., by the relative ratio of hPG and functionalization compound used in the functionalization reaction. In FIGS. 3A, 3B and 3C, only a single catecholic group linked via a linker or spacer moiety to a polyglycerol core is indicated. It is, however, obvious for a person skilled in the art that the depicted chemical reactions can result in hPGs carrying more than one catecholic group per polamer molecule if the reaction conditions are properly chosen.

Once a catechol-functionalized polymer is prepared, this functionalized polymer has to be applied onto a substrate in order to produce an article. In case of the articles schematically depicted in FIGS. 1A and 1B, the coatings of hPG-Cat10 and hPG-Cat1 were prepared at pH 7.5 in 3-(N-morpholino)propanesulfonic acid buffer (MOPS) with a concentration of hPG-Cat10 or hPG-Cat1 of 1 mmol/l. The coatings of hPG(NH$_2$)Cat40 were prepared in a mixed solution of methanol and MOPS buffer (4:1, v/v) at pH 8.5 with a concentration of hPG(NH$_2$)Cat40 of 0.1 mmol/l.

Figure 4A:
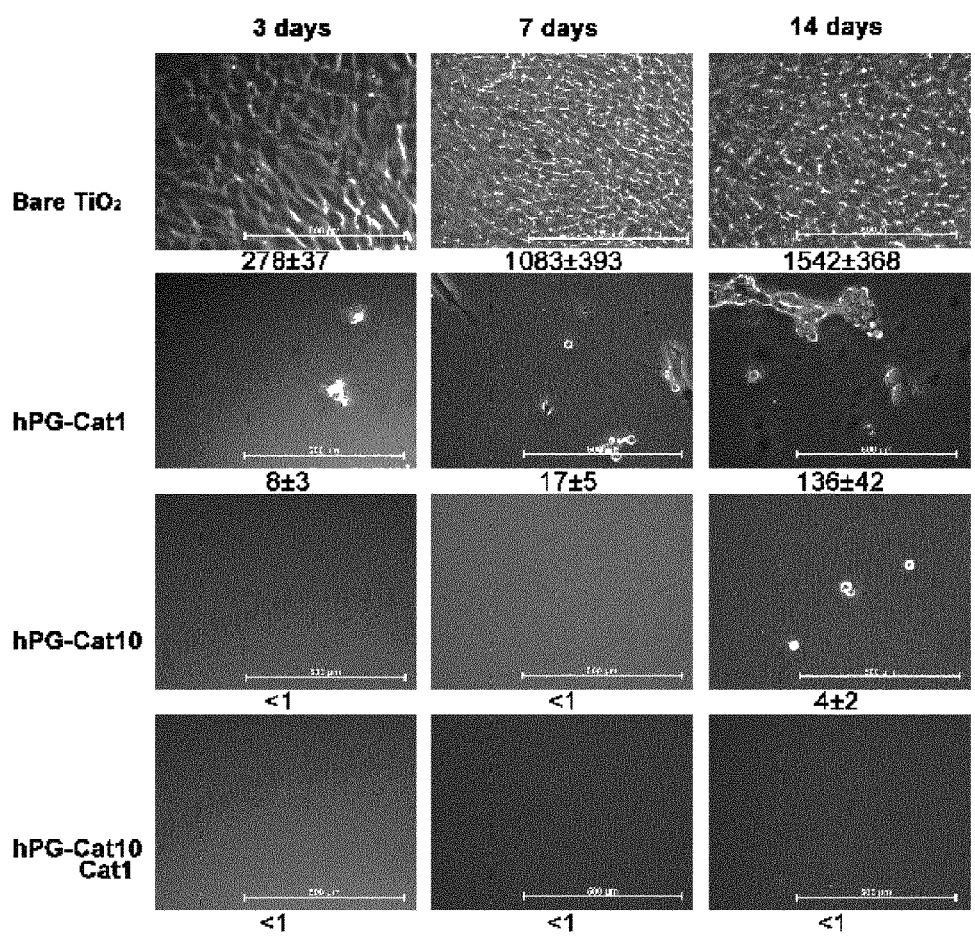
FIG. 4A shows micrographs obtained by a light-optical microscope of a first cell-adhesion experiment.

FIG. 4A shows light microscopic micrographs of a cell culture experiment with hPG-Cat-modified and unmodified surfaces to study cell adhesion of NIH-3T3 mouse fibroblasts.

The Fibroblasts were collected from Petri dishes by incubation in trypsin (dilution 1:250) for 5 minutes at 37° C. The cell suspension was washed from trypsin by centrifugation, the top layer was removed, and the remaining cells were resuspended in fresh medium. Surface-modified and non-modified slides were incubated with 1 million cells in 4 ml of cell medium (cell number was determined via a Neubauer chamber) for 3, 7 and 14 days respectively, at 37° C. and 5% CO$_2$. The medium for cell culture was changed to fresh every two days. After removing the medium and rinsing the slides with 4 ml phosphate-buffered saline (PBS) to remove non-adherent cells, the remaining cells were observed directly by microscope (TELAVAL 31, Zeiss, Germany). The average number of the adhering cells was calculated from at least five randomly chosen areas.

The first row of FIG. 4A shows the cell adhesion in case of bare titanium dioxide substrates. The second row shows the cell adhesion on substrates that have been coated with hPG-Cat1 only. The third row shows the cell adhesion of substrates that have been coated with hPG-Cat10 only. The fourth and last row shows the cell adhesion of substrates that have been coated with a two-layer polymer film consisting of a foundation layer of hPG-Cat10 and a sealing top layer of hPG-Cat1. As can be clearly seen from the micrographs of FIG. 4A, the two-layer architecture of the fourth row is the only one which ensures no cell adhesion even after 14 days.

After 3 days of cultivation, cells spread regularly on the unmodified titanium dioxide surfaces (278±37 cells/mm$^2$), whereas only small amounts of cell colonies could be observed on the hPG-Cat1 modified surfaces (8±3 cells/mm$^2$), but almost no cells could be detected on the hPG-Cat10 and hPG-Cat10Cat1 modified surfaces.

After 7 days, more cells were growing on the hPG-Cat1 modified surfaces (17±5 cells/mm$^2$), while the hPG-Cat10 and hPG-Cat10Cat1 modified surfaces still showed no cell attachment.

After 14 days of incubation, the surfaces of unmodified titanium dioxide was very confluently covered, the mean cell number reached 1542±368 cells/mm$^2$ and the cell colonies on the hPG-Cat1 modified surfaces grew much larger than before (136±42 cells/mm$^2$). Meanwhile, a few cells adhered on the hPG-Cat10 modified surfaces with only 4±2 cells/mm$^2$ and still almost no cells could adhere to the hPG-Cat10Cat1 modified surfaces (<1 cells/mm$^2$).

Since hPG-Cat1 with only one catechol anchor is not stable enough to cover the surface very effectively, its coating showed weaker antifouling performance than hPG-Cat10. However, the free catechols on the surface of hPG-Cat10 multilayers still led to some protein adsorption and cell adhesion. When these free catechols were covered by hPG-Cat1 as the terminal layer, the substrates were perfectly protected by the hPG bioinert coatings and showed only very weak interaction with proteins and cells. The long-term cell culture tests also proved the stability of the hPG-Cat10Cat1 dual layer, which was enhanced by both multivalent adhesion (anchoring) and cohesion (crosslinking).

Figure 4B:
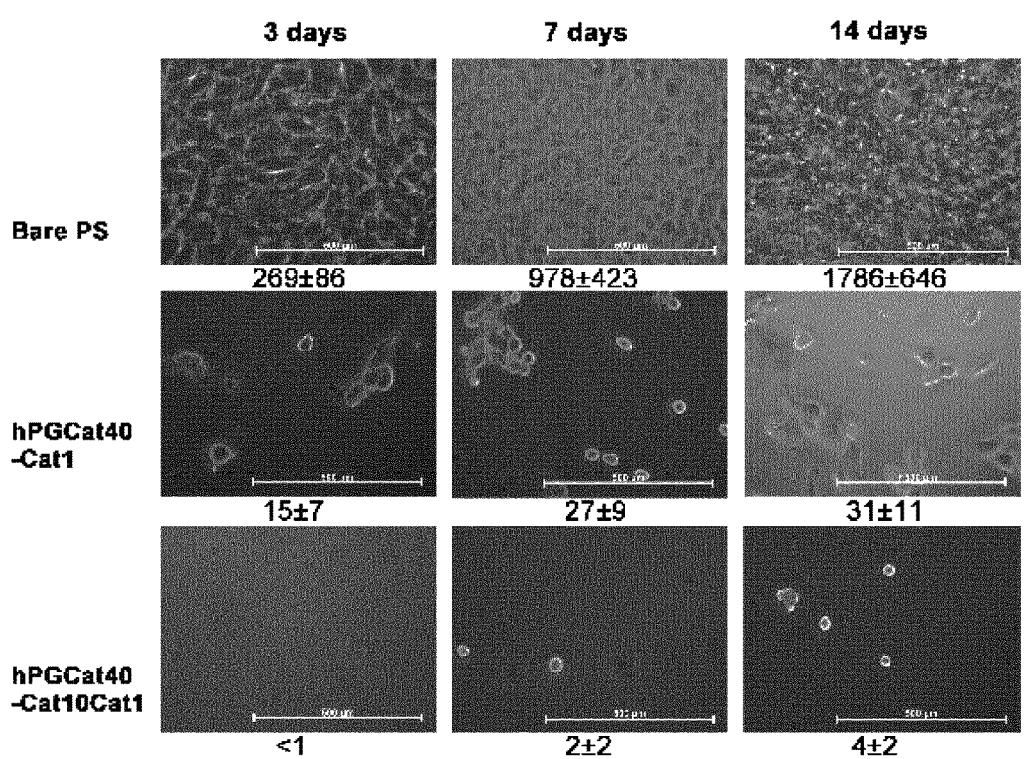
FIG. 4B shows micrographs obtained by a light-optical microscope of a second cell-adhesion experiment.

FIG. 4B shows light microscopic micrographs of cell adhesion experiments performed on Petri dishes made of polystyrene (PS). The first row shows the results with respect to bare PS as substrate. The second row shows the results in case of a PS substrate coated with a two-layered polymer film made up of hPG(NH$_2$)Cat40 (abbreviated in FIG. 4B as hPG-Cat40) as foundation layer and hPG-Cat1 as top layer. The third and last row shows the results with respect to a PS substrate coated by a three-layered polymer film made up of hPG(NH$_2$)Cat40 as foundation layer, hPG-Cat10 as intermediate layer and hPG-Cat1 as top layer.

The condition of modified PS Petri dishes was similar as modified titanium dioxide surfaces. Cells on unmodified surfaces spread regularly after 3 days and grew to confluence after 14 days. A considerable amount of cells adhered on the hPG(NH$_2$)Cat40-hPG-Cat1 coated surfaces. But unlike the hPG-Cat1 coatings on titanium dioxide surfaces, the cell number did not increase too much from 7 days to 14 days (from 27±9 to 31±11 cells/mm$^2$). Instead, all cells completely spread on the surfaces. That may be because the hPG-Cat1 layers on hPG(NH$_2$)Cat40 treated surfaces are more stable than on bare titanium dioxide surfaces, but cannot fully shield the foundation layer. There were only a few cells on the hPG(NH$_2$)Cat40-hPG-Cat10-hPG-Cat10 modified surfaces (4±2 cells/mm$^2$) after 14 days. As comparison, hPG-Cat10 alone coated and hPG(NH$_2$)Cat40 coated PS surfaces were incubated with cells for 3 days. 229±104 and 729±329 cells/mm$^2$ adhered on the respective surfaces.

It can clearly be seen that the best results can be obtained with a three-layered architecture. By using a PS surface coated with such a three-layer polymer film, only a very low number of cells adheres to the surface within 14 days after incubation. But also in case of a two-layered architecture very good results can be obtained with respect to the uncoated control experiment.

Figure 5:
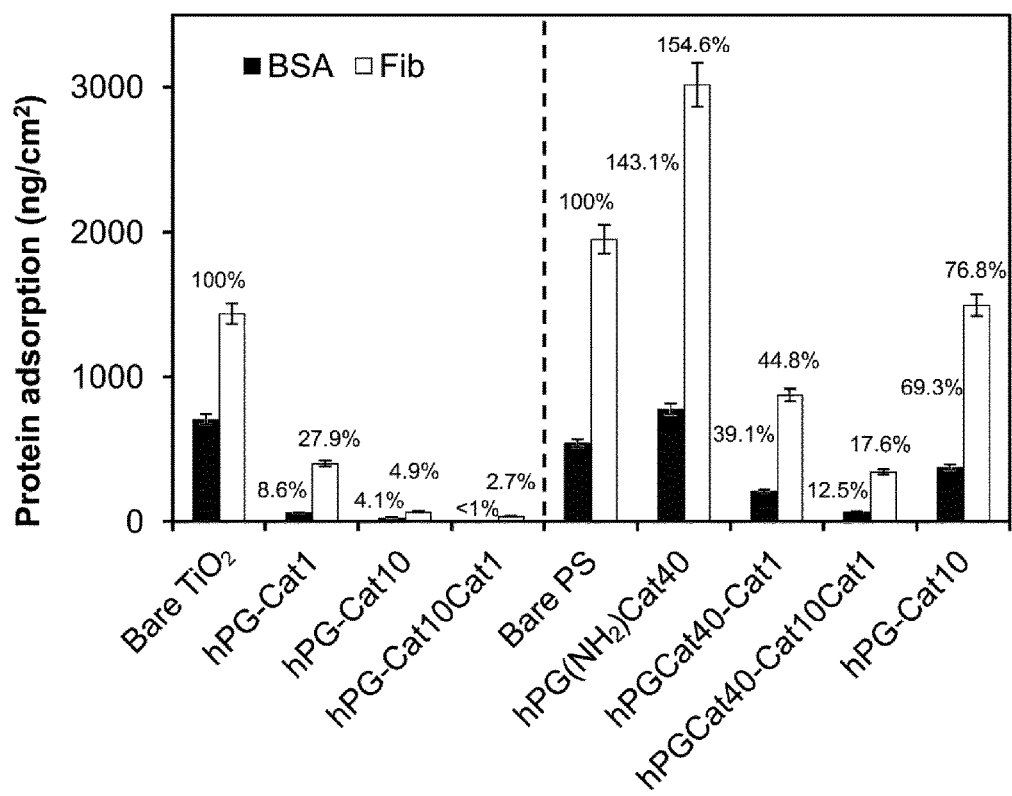
FIG. 5 is a graphical depiction of the results obtained from protein adsorption experiments on fresh coatings.

FIG. 5 shows the results of protein adsorption experiments performed on coated and uncoated titanium dioxide and polystyrene. Bovine serum albumin (BSA) and fibrinogen (Fib) were used as proteins in these experiments. The single protein resistance of the substrates was evaluated by quartz crystal microbalance (QCM) measurements. Additionally, the obtained data was fitted into the Kevin-Voigt model to quantify the amount of adsorbed proteins. FIG. 5 shows the adsorbed amount of BSA and Fib on titanium dioxide (left) and PS (right) surfaces. The adsorption of BSA and Fib on bare titanium dioxide and on bare polystyrene has been set to 100%.

Both hPG-Cat1 and hPG-Cat10 modified titanium dioxide surfaces showed an improved resistance against the adsorption of BSA and Fib compared to an unmodified surface. However, the hPG-Cat1 coating without any catechols on the top still adsorbed 8.6% of BSA and 27.9% of Fib, which were much more than the hPG-Cat10 coating (4.1% for BSA and 4.9% for Fib). By hiding the free catechols on the surface of hPG-Cat10 layer, the hPG-Cat10Cat1 dual layer architecture had such excellent antifouling performance that only 2.7% of the Fib and <1% of the BSA were adsorbed relative to the bare titanium dioxide. This is particular surprising when considering the results obtained with hPG-Cat1 alone.

However, 10% of catechol groups obviously cannot tether the hPG sufficiently stably on PS surfaces, which lead the strong adsorption of BSA (69.3%) and Fib (76.8%). Thus, the triple layer coatings with more active foundation layer can be advantageously used to modify chemical inert surfaces like PS surfaces. Although a hPG(NH$_2$)Cat40 foundation layer increased about 50% of protein adsorption, it successfully immobilized an inert hPG-Cat1 layer to decrease the protein adsorption. hPG-Cat1 crosslinked multilayer shielded the hPG(NH$_2$)Cat40 foundation layer already quite effectively (39.1% for BSA and 44.8% for Fib).

By further grafting hPG-Cat1 on free catechol groups of a hPG-Cat10 layer, a triple layer was generated that only adsorbed 12.5% of the BSA and 17.6% of the Fib relative to the bare PS.

After incubation of the dual layer coated titanium dioxide slides and triple layer coated PS slides in 4-(2-hydroxyethyl)-1-piperazineethanesulfonic acid (HEPES) buffer (physiological condition) for two weeks, the Fib adsorption on the respective surfaces only slightly increased to 3.5% (dual layer coated titanium dioxide) and 20.1% (triple layer coated PS slides) respectively. Thus, the cohesion enhanced coatings showed very good stability in physiological buffer.

Summarizing, the lowest protein adsorption can be observed in case of titanium dioxide coated with a two-layered polymer film consisting of hPG-Cat10 and hPG-Cat1. In case of polystyrene, the lowest protein adsorption can be observed for polystyrene coated with a three-layer polymer film consisting of hPG-Cat40, hPG-Cat10 and hPG-Cat1.

These protein adsorption tests clearly show that polymer-film coated substrates behave in a bioinert manner as compared to non-coated substrates.

Figure 6:
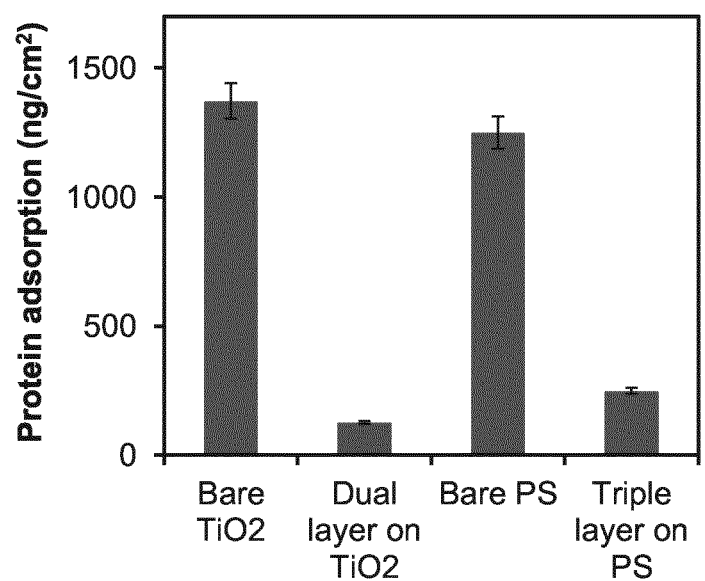
FIG. 6 is a graphical depiction of the results obtained from protein adsorption from undiluted human blood plasma on polymer-coated articles.

The protein adsorption in a highly complex protein environment of undiluted human blood plasma was tested on dual layer coated TiO$_2$ surfaces and triple layer coated PS surfaces, each built up as explained above with respect to FIGS. 1A and 1B. The results are shown in FIG. 6.

It was previously shown that unspecific protein adsorption from the highly complex protein mixture in plasma cannot be reduced substantially by many of the current benchmarks of protein-resistant polymer coated surfaces. [G. Gunkel, W. T. S. Huck. J. Am. Chem. Soc. 2013, 135, 7047.]

The multilayer surfaces adsorbed small to moderate amounts of proteins from undiluted plasma, however, significantly less (more than 5-fold reduced) as compared to the bare surface. The dual layer coatings on TiO$_2$ decreased the amount of adsorbed proteins to 9% compared to the adsorption on bare TiO$_2$ (100% adsorption) surfaces. The triple layer coatings on PS decreased plasma adsorption to 20% compared to bare PS (100% adsorption) surfaces. Thus, these new multilayer coatings reduce protein adsorption from highly complex protein mixtures like undiluted plasma to a significant level and show even better performance than a self-assembled monolayer (SAM) of polyether glycol on gold. [M. Weinhart, I. Grunwald, M. Wyszogrodzka, L. Gaetjen, A. Hartwig, R. Haag. Chem.-Asian J. 2010, 5, 1992.]

Figure 7:
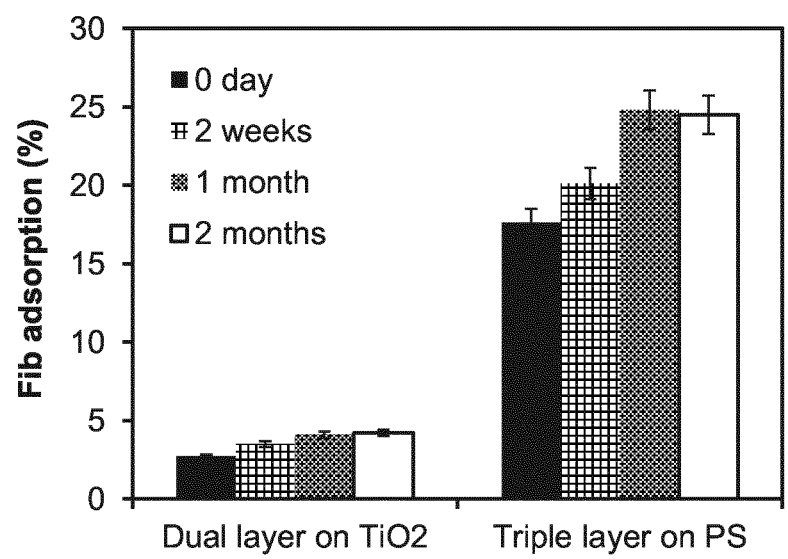
FIG. 7 is a graphical depiction of the results obtained from protein adsorption experiments on polymer-coated articles which have been exposed to a physiological environment (physiological buffer) for different periods of time.

The long term stability of the dual layer and triple layer coatings in physiological buffer (pH 7.4 HEPES buffer) was tested by Fib adsorption. The results are shown in FIG. 7. The adsorption on dual layer coated titanium oxide surfaces only slightly increased from 2.7% to 3.5% after two weeks of incubation, and to 4.2% after two months of incubation. The adsorption on triple layer coated PS surfaces increased moderately from 17.6% to 20.1% after two weeks, and 24.5% after two months. Hence, the crosslinked multilayer architecture showed good stability in physiological buffer conditions. An obvious thickness decreasing can be observed after only 12 days in the case of the monolayer of catecholic PEG dendrons on titanium oxide surfaces. It should be noticed that any defect on the monolayer surfaces may cause protein adsorption.

The invention claimed is:

1. An article, comprising:
a substrate; and
a polymer film attached to the substrate, the polymer film comprising:
a first layer of a first polymer functionalized by a first functionalization compound covalently bound to said first polymer and bearing at least one catecholic group being present on a surface of the first layer,
wherein the polymer film is a layered film, a top layer of which is formed by the first layer, the layered film comprising at least one further layer of at least one further polymer functionalized by a further functionalization compound covalently bound to said further polymer and bearing at least one catecholic group being present on a surface of the at least one further layer,
wherein an average ratio of catecholic groups per polymer molecule is equal to or less than 1 in a case of the first polymer and greater than 1 in a case of the further polymer,
wherein the first polymer and/or the further polymer has, besides the catecholic groups, reactive groups that can be functionalized in order to adjust physical and/or chemical surface properties of the article, wherein the reactive groups are amine, amide, azide and/or sulfhydryl groups.

2. The article according to claim 1, wherein a lowest polymer layer of the layered polymer film is covalently or non-covalently attached to the substrate.

3. The article according to claim 1, wherein the further polymer is covalently or non-covalently bound to a polymer of a polymer layer of the layered polymer film that is placed directly above the further polymer layer.

4. The article according to claim 1, wherein the further polymer has a degree of functionalization with catecholic groups of 1 to 100%.

5. The article according to claim 1, wherein the first polymer and/or the further polymer is at least one of the group consisting of polyglycerols, polyethers, polyethylene glycols, polyesters, polyamides, polyimides, polyimines, polyurethanes, polycarbonates, polyethersulfones, oligopeptides, polypeptides and copolymers thereof, in each case functionalized by the first or the further functionalization compound.

6. The article according to claim 1, wherein the first polymer and/or further polymer has a molecular weight of 0.3 to 6000 kDa after functionalization, determined by gel permeation chromatography.

7. The article according to claim 1, wherein the first and/or further functionalization compound has a linker moiety through which the catecholic group is bound to the first polymer and/or further polymer.

8. The article according to claim 1, wherein the first polymer is additionally functionalized with at least one compound selected from the group consisting of polyethylene glycol, oligoethylene glycol, zwitterionic moieties, polyoxazolines, oligooxazolines, and other hydrophilic groups based on amides, amide derivatives, cyclic esters, sugar derivatives, amino acids and/or oligonitrils.

9. The article according to claim 1, wherein the first polymer is additionally functionalized with at least one compound selected from the group consisting of bioactive units or ligands such as amino acids, peptides, monosaccharides, oligosaccharides, polysaccharides, proteins, DNA and RNA.

10. The article according to claim 1, wherein the first functionalization compound and the further functionalization compound are identical.

11. The article according to claim 1, wherein the layered polymer film has a thickness of 1 nm to 100 μm.

12. The article according to claim 1, wherein the substrate comprises at least one compound chosen from the group consisting of $TiO_2$, aluminum, glass, $SiO_2$, polystyrene, polypropylene and polyvinyl chloride.

13. A method for in vitro cell culturing, wherein an article is used as a cell culture device, wherein the article comprises:
a substrate; and
a polymer film attached to the substrate, the polymer film comprising:
a first layer of a first polymer functionalized by a first functionalization compound covalently bound to said first polymer and bearing at least one catecholic group being present on a surface of the first layer,
wherein the polymer film is a layered film, a top layer of which is formed by the first layer, the layered film comprising at least one further layer of at least one further polymer functionalized by a further functionalization compound covalently bound to said further polymer and bearing at least one catecholic group being present on a surface of the at least one further layer, wherein an average ratio of catecholic groups per polymer molecule is equal to or less than 1 in case of the first polymer and greater than 1 in case of the further polymer.

14. A method of implantation of an implantable device, wherein an article is used as an implantable device or as part of an implantable device, wherein the article comprises:
a substrate; and
a polymer film attached to the substrate, the polymer film comprising:
a first layer of a first polymer functionalized by a first functionalization compound covalently bound to said first polymer and bearing at least one catecholic group being present on a surface of the first layer,
wherein the polymer film is a layered film, a top layer of which is formed by the first layer, the layered film comprising at least one further layer of at least one further polymer functionalized by a further functionalization compound covalently bound to said further polymer and bearing at least one catecholic group being present on a surface of the at least one further layer, wherein an average ratio of catecholic groups per polymer molecule is equal to or less than 1 in case of the first polymer and greater than 1 in case of the further polymer.

15. The method according to claim 14, wherein the device is intended for permanent implantation.

16. The method according to claim 14, wherein the device is intended for non-permanent implantation.

17. An article, comprising:
a substrate; and
a polymer film attached to the substrate, the polymer film comprising:
a first layer of a first polymer functionalized by a first functionalization compound covalently bound to said first polymer and bearing at least one catecholic group being present on a surface of the first layer,
wherein the polymer film is a layered film, a top layer of which is formed by the first layer, the layered film comprising at least one further layer of at least one further polymer functionalized by a further functionalization compound covalently bound to said further polymer and bearing at least one catecholic group being present on a surface of the at least one further layer, wherein an average ratio of catecholic groups per polymer molecule is equal to or less than 1 in a case of the first polymer and greater than 1 in a case of the further polymer,
wherein the substrate comprises at least one compound chosen from the group consisting of $TiO_2$, aluminum, glass, $SiO_2$, polystyrene, polypropylene and polyvinyl chloride.

18. The article according to claim 17, wherein a lowest polymer layer of the layered polymer film is covalently or non-covalently attached to the substrate.

19. The article according to claim 17, wherein the further polymer is covalently or non-covalently bound to a polymer of a polymer layer of the layered polymer film that is placed directly above the further polymer layer.

20. The article according to claim 17, wherein the first polymer and/or the further polymer is at least one of the group consisting of polyglycerols, polyethers, polyethylene glycols, polyesters, polyamides, polyimides, polyimines, polyurethanes, polycarbonates, polyethersulfones, oligopeptides, polypeptides and copolymers thereof, in each case functionalized by the first or the further functionalization compound.

21. The article according to claim 17, wherein the first polymer and/or further polymer has a molecular weight of 0.3 to 6000 kDa after functionalization, determined by gel permeation chromatography.

22. The article according to claim 17, wherein the first and/or further functionalization compound has a linker moiety through which the catecholic group is bound to the first polymer and/or further polymer.

23. The article according to claim 17, wherein the first polymer is additionally functionalized with at least one compound selected from the group consisting of polyethylene glycol, oligoethylene glycol, zwitterionic moieties, polyoxazolines, oligooxazolines, and other hydrophilic groups based on amides, amide derivatives, cyclic esters, sugar derivatives, amino acids and/or oligonitrils.

24. The article according to claim 17, wherein the first polymer is additionally functionalized with at least one compound selected from the group consisting of bioactive units or ligands such as amino acids, peptides, monosaccharides, oligosaccharides, polysaccharides, proteins, DNA and RNA.

* * * * *